United States Patent
Young

(10) Patent No.: US 11,491,190 B2
(45) Date of Patent: Nov. 8, 2022

(54) VISCO-SUPPLEMENT COMPOSITIONS, AND METHODS OF USE THEREOF

(71) Applicant: Prime Merger Sub, LLC, Birmingham, AL (US)

(72) Inventor: Robin R. Young, Wayne, PA (US)

(73) Assignee: Prime Merger Sub, LLC, Birmingham, AL (US)

( * ) Notice: Subject to any disclaimer, the term of this patent is extended or adjusted under 35 U.S.C. 154(b) by 0 days.

(21) Appl. No.: 16/944,059

(22) Filed: Jul. 30, 2020

(65) Prior Publication Data

US 2020/0353013 A1    Nov. 12, 2020

Related U.S. Application Data

(63) Continuation of application No. 14/950,186, filed on Nov. 24, 2015, now Pat. No. 10,765,705.

(60) Provisional application No. 62/083,606, filed on Nov. 24, 2014.

(51) Int. Cl.
| | | |
|---|---|---|
| A61K 36/00 | (2006.01) | |
| A61K 35/50 | (2015.01) | |
| A61K 9/00 | (2006.01) | |
| A61K 45/06 | (2006.01) | |
| A61K 35/30 | (2015.01) | |

(52) U.S. Cl.
CPC ............ *A61K 35/50* (2013.01); *A61K 9/0019* (2013.01); *A61K 35/30* (2013.01); *A61K 45/06* (2013.01)

(58) Field of Classification Search
None
See application file for complete search history.

(56) References Cited

PUBLICATIONS

Karacal et al. (2005) J. Surg. Res. 129: 283-287. (Year: 2005).*
Barbucci et al. (2002) Biomaterials 23: 4503-4513. (Year: 2002).*
Shimberg (1938) J. Bone and Joint Surgery vol. XX, No. 1: 167-177. (Year: 1938).*

* cited by examiner

*Primary Examiner* — Russell G Fiebig
(74) *Attorney, Agent, or Firm* — C. Brandon Browning; Maynard, Cooper & Gale, PC

(57) ABSTRACT

Visco-supplement compositions derived from a transcellular fluid, such as human amniotic fluid, human aqueous humor fluid, or human vitreous fluid are described. Also described are methods for treating inflammatory conditions of the musculoskeletal system, such as joint inflammation, and methods of lubricating a joint using the described visco-supplement compositions.

19 Claims, No Drawings

VISCO-SUPPLEMENT COMPOSITIONS, AND METHODS OF USE THEREOF

CROSS REFERENCE TO RELATED APPLICATIONS

This application is a continuation of U.S. application Ser. No. 14/950,186 filed on Nov. 24, 2015 titled "Visco-Supplement Compositions, and Methods of Use Thereof", which claims priority to U.S. Provisional Patent Application No. 62/083,606, filed Nov. 24, 2014, the entire contents of which are incorporated herein by reference.

FIELD OF INVENTION

The present invention relates to visco-supplement compositions derived from a transcellular fluid. The present invention also relates to methods of treating an inflammatory condition of the human musculoskeletal system, such as joint inflammation or osteoarthritis, and increasing joint lubrication with the visco-supplement compositions described herein.

BACKGROUND OF INVENTION

Visco-supplements are viscous substances that can function as a lubricant and shock absorber for joints, and are often used to treat inflammatory conditions of the human musculoskeletal system. Many visco-supplements typically used for treating inflammatory conditions of the human musculoskeletal system are produced via bacterial culturing, or by a process of extraction from tissues of a different species, such as rooster combs, which is the fleshy growth on top of the rooster's head.

The primary viscous, protecting, nutritional and lubricating fluid of the human musculoskeletal system responsible for maintaining healthy, articulating joints is synovial fluid. Synovial fluid is secreted by the synovial membrane, which is the soft tissue found between the articular capsule (joint capsule) and joint cavity. In native joints, synovial fluid functions as a biomechanical lubricant, lowering the friction and wear of articulating cartilage in joints, as well as a source of nutrients for the articulating tissues. Synovial fluid lubricating macromolecules, including hyaluronic acid and proteoglycan 4 (PRG4), are secreted by synoviocytes in the synovial membrane lining the joint and chondrocytes in the cartilage of the joint, and are concentrated in synovial fluid due to the retaining property of the semi-permeable synovial membrane.

Currently available visco-supplements for the treatment of inflammatory conditions of the human musculoskeletal system are comprised of essentially a single component, hyaluronic acid (HA). Considering the complexity of naturally occurring synovial fluid, and the complex biological system necessary for maintaining the health and proper functioning of articulating joints, pure HA is not an ideal treatment for inflamed joints at least for physiological reasons.

Furthermore, the clinical record of currently available HA based visco-supplements is poor. That record was recently reviewed by the American Academy of Orthopedic Surgeons (AAOS), and in June, 2013, the AAOS issued clinical practice guidelines to physicians, which recommended against using HA for patients with symptomatic osteoarthritis (OA) of the knee based on supporting evidence from several high-quality research studies that met the inclusion criteria.

The AAOS's clinical practice guidelines are based on some of the best peer reviewed study evidence available. According to the AAOS's website, currently published studies do not show a clinically effective response for HA injections based on minimal clinically important improvements (MCIIs). Some peer reviewers were critical of the AAOS' findings and recommendation, especially in light of the important clinical practice implications, and highlighted prior systematic reviews supporting the use of HA. However, these reviews were analyzed and found to have several flaws. For example, most did not address the issues of publication bias, between-study heterogeneity, and clinical significance in determining final recommendations.

Inflammation of articulating surfaces of the musculoskeletal system is one of the most common medical complaints. Although the exact causes for painful knee, hip, shoulder, facet, ankle and wrist joints may be difficult to ascertain and in many cases are unknown, it is understood that degenerative damage, especially cartilage damage, plays a central role in the pathogenic mechanism leading to this disorder. Current treatment modalities include pharmacological treatments, physiotherapy, visco-supplement injections, corticosteroid injections and, at the terminus of a continuum of care for joint pain, surgical replacement of the joint. According to the Centers for Disease Control (CDC), nearly one in two people are projected to develop symptomatic knee osteoarthritis by age 85 years; two in three people who are obese are projected to develop symptomatic knee osteoarthritis in their lifetime; and one in four people are projected to develop hip arthritis in their lifetime. Also, according to the CDC, an estimated 52.5 million adults in the United Stated reported being told by a doctor that they have some form of arthritis, rheumatoid arthritis, gout, lupus, or fibromyalgia.

Moreover, by 2030, the number of Americans aged 18 years or older who are projected to have doctor-diagnosed arthritis is 67 million.

Present pharmacological treatments for such joint inflammation include the use of non-steroidal anti-inflammatory drugs (NSAIDs), such as naproxen, ibuprofen, etc., and drugs of the cyclooxygenase-2 inhibitor group like celecoxib, as well as other drugs including glucosamine, chondroitin, and opiates. Present non-pharmacological treatments include hot or cold packs around the inflamed joint; anaerobic exercises, such as resistance training; suggestion of weight loss or use of a crutch; use of a brace, particularly for the patella; and correction of joint tiling or misalignment.

However, many of the pharmacological and non-pharmacological treatments employed for treating joint inflammation suffer from several drawbacks. For example, corticosteroid injections are one of the most common anti-inflammatory treatments for joint pain, and it carries many risks including deteriorating articulating cartilage in the joint if overused, atrophy of subcutaneous fat, and nerve inflammation. There is, as a result, growing interest in the development of novel technologies to repair or regenerate the painful, degenerated articulating musculoskeletal bone and cartilage system.

Accordingly, there exists a need in the art for improved methods and compositions for treating inflammation of the human musculoskeletal system. Preferably, such improved compositions provide the requisite lubrication, cushioning, and protection of the joint, but more closely resemble the composition of synovial fluid found in healthy articulating joints as compared to known visco-supplements.

BRIEF SUMMARY OF INVENTION

The present invention satisfies this need by providing a visco-supplement that can be used to treat inflammation of the human musculoskeletal system, and particularly joint inflammation. The visco-supplement of the present invention, which is a processed transcellular fluid, provides not only the requisite lubrication, cushioning, and protection of the joint, but also the components and pH level required for maintaining the healthy biological and physiological function of the entire joint system.

In one general aspect, the present invention provides a visco-supplement composition. According to embodiments of the present invention, the visco-supplement composition comprises a processed transcellular fluid, wherein the processed transcellular fluid comprises:

(a) an increased concentration of at least one of a first component selected from the group consisting of proteins, lipids, and carbohydrates as compared to a concentration in an unprocessed transcellular fluid; and (b) a decreased concentration of at least one of a second component selected from the group consisting urea, uric acid, and creatinine, as compared to a concentration in the unprocessed transcellular fluid, and the composition has a pH in a range of about 6.0 to about 8.0.

In a preferred embodiment, the unprocessed transcellular fluid is a human transcellular fluid. In another preferred embodiment, the unprocessed transcellular fluid is selected from the group consisting of an amniotic fluid (AF), aqueous humor fluid (AHF), and vitreous humor fluid.

In another general aspect, the present invention provides a method of treating an inflammatory condition of a musculoskeletal system in a subject in need of treatment thereof. According to embodiments of the present invention, the method comprises injecting a visco-supplement composition according to an embodiment of the present invention into the musculoskeletal system of the subject. Preferably, the inflammation of the musculoskeletal system is joint inflammation, and more preferably inflammation of the knee joint, such as osteoarthritis of the knee.

In a particular embodiment, the present invention provides a method of treating joint inflammation in a knee in a subject in need thereof, the method comprising administering to the knee of the subject, a visco-supplement composition comprising a processed human amniotic fluid, wherein the processed human amniotic fluid comprises:

(a) an increased concentration of at least one of a first component selected from the group consisting of proteins, lipids, and carbohydrates as compared to a concentration in an unprocessed human amniotic fluid; and (b) a decreased concentration of at least one of a second component selected from the group consisting urea, uric acid, and creatinine, as compared to a concentration in the unprocessed human amniotic fluid, wherein the composition has a pH in a range of about 6.0 to about 8.0, and wherein the administration comprises intra-articular injection to the knee.

In another particular embodiment, the subject to be treated has osteoarthritis, thereby causing the joint inflammation in the knee.

In yet another general aspect, the present invention provides a method of lubricating a joint in a subject in need thereof. The method comprises injecting into an articular capsule of the joint in the subject a visco-supplement composition according to an embodiment of the present. In a preferred embodiment, the joint is a knee joint.

Other aspects, features and advantages of the invention will be apparent from the following disclosure, including the detailed description of the invention and its preferred embodiments and the appended claims.

DETAILED DESCRIPTION OF INVENTION

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

As used herein, "visco-supplement" refers to a viscous or gel-like fluid that can function as a replacement for, or supplement to, a natural fluid present in a musculoskeletal system, such as a synovial fluid.

As used herein, "transcellular fluid" is the portion of the body water which is contained within epithelial lined spaces. It is an ultra-filtrate of blood plasma, and is derived from blood plasma. Examples of transcellular fluids are aqueous humour, blood serum, amniotic fluid, cerebrospinal fluid, sweat, tears, synovial fluid, ocular fluid, pericardial fluid, vitreous humour, bile, saliva, semen, vaginal lubrication, breast milk, mucus, and urine. Transcellular fluids typically have specialized functions, which depend upon the particular location of the body that the transcellular fluid is found.

"Synovial fluid," as used herein, refers to the viscous fluid found in the cavities of synovial joints. Synovial fluid is also referred to as "joint fluid." Synovial fluid is secreted by the synovial membrane, which is the inner membrane lining a synovial joint. The primary role of synovial fluid is to reduce friction between articular cartilage of synovial joints during movement. Synovial fluid has other functions, including, but not limited to, reducing joint friction through lubrication, shock absorption, and nutrient and waste transportation.

As used herein, "aqueous humor fluid" generally refers to the transcellular fluid secreted into the posterior chamber of the eye. "Vitreous humor fluid" generally refers to the fluid found in the vitreous of the eye, which is the space between the lens and retina of the eyeball.

As used herein, "amniotic fluid" refers to the fluid contained inside the membrane that forms a protective sac around the embryo and later the fetus, in a pregnant female. The placenta itself acts as a filter for blood plasma and produces the amniotic fluid.

The term "unprocessed," when used with respect to a transcellular fluid, refers to a transcellular fluid that has not been treated, such that it has substantially the same composition, i.e., same components in the same amounts, as the native transcellular fluid found in vivo.

The term "processed," when used with respect to a transcellular fluid, means that the transcellular fluid has been treated, such that it has an altered composition as compared to the native transcellular fluid found in vivo. In one embodiment, a processed transcellular fluid has one or more different components, such as proteins, lipids, and carbohydrates, as compared to the unprocessed transcellular fluid. In another embodiment, a processed transcellular fluid has the same components, such as proteins, lipids, and carbohydrates, as compared to the unprocessed transcellular fluid, but the components are present in different amounts, i.e., in an increased concentration or a decreased concentration. In another embodiment, a processed transcellular fluid has a different viscosity as compared to the unprocessed transcellular fluid.

Embodiments of the present invention relate to a visco-supplement composition that is an enriched composition of a transcellular fluid for use in treating an inflammatory condition of the musculoskeletal system, such as joint inflammation, and for lubricating a joint. The visco-supplement composition of the present invention more closely approximates the composition of synovial fluid as compared to conventional visco-supplements and other injection materials used to treat inflammatory conditions of the musculoskeletal system and joint inflammation.

In one general aspect, the present invention provides a visco-supplement composition comprising a processed transcellular fluid. The processed transcellular fluid can be derived from any transcellular fluid described herein, and is preferably an amniotic fluid, aqueous humor fluid, or vitreous humor fluid.

According to preferred embodiments, the transcellular fluid is a human amniotic fluid, a human aqueous humor fluid, or a human vitreous humor fluid. In a particularly preferred embodiment, the transcellular fluid is a human amniotic fluid, and more preferably is human amniotic fluid harvested from a pregnant female undergoing either Caesarean delivery or vaginal birth. Preferably, the technique used for harvesting the amniotic fluid should substantially eliminate, or at least minimize, the presence of red blood cells in the amniotic fluid. Furthermore, the amniotic fluid used in the present invention should not be cloudy in color, and it should not have any particulate matter.

According to embodiments of the present invention, the concentrations of the components found in the unprocessed transcellular fluid, particularly inorganic constituents, gases, non-protein nitrogenous compounds, proteins, carbohydrates, and lipids, differ from the concentrations found in the processed transcellular fluid. The concentration of any one particular component in the processed transcellular fluid can be increased, decreased, or unchanged as compared to the concentration in the unprocessed transcellular fluid, independent of any other component. For example, the concentration of creatinine in the processed transcellular fluid can be decreased, whereas the concentration of glucose can be increased, as compared to their respective concentrations in the unprocessed transcellular fluid.

According to embodiments of the present invention, the processed transcellular fluid comprises an increased concentration of at least one of a first component selected from the group consisting of proteins, lipids, and carbohydrates as compared to a concentration in an unprocessed transcellular fluid; and a decreased concentration of at least one of a second component selected from the group consisting urea, uric acid, and creatinine, as compared to a concentration in the unprocessed transcellular fluid.

In one general aspect a visco-supplement composition according to the present invention comprises a processed transcellular fluid having increased concentrations of proteins as compared to the unprocessed transcellular fluid. According to embodiments of the present invention, the total protein concentration is increased in the processed transcellular fluid, such that the aggregate protein content ranges from about 30.25 g/L to about 50.375 g/L. The concentrations of at least one of cytokines, such as interleukin (IL)-6, IL-8, IL-1β, and tumor necrosis factor (TNF)-α, are increased in the processed transcellular fluid; and the concentrations of at least one of globulins, such as .alpha.-globulins, .beta.-globulins, and .gamma.-globulins, are increased as compared to their concentrations in the unprocessed transcellular fluid. According to other embodiments of the invention, albumin comprises no less than 60% of the total protein content in the processed transcellular fluid. Also according to embodiments of the present invention, the concentration of other proteins present in the unprocessed transcellular fluid, such as C-reactive protein, procalcitonin, and/or calprotectin can be present in the processed transcellular fluid, or they can be eliminated.

In preferred embodiments of the present invention, in the processed transcellular fluid, the concentration of α-globulins is at least 12% of the total protein concentration, preferably 12% to 18%; the concentration of β-globulins is at least 16% of the total protein concentration, preferably 16% to 27%; and the concentration of γ-globulins is at least 12% of the total protein concentration, preferably 12% to 18%. In other preferred embodiments, in the processed transcellular fluid, the concentration of IL-6 is at least 329 ng/L, the concentration of IL-8 is at least 421 ng/L, the concentration of IL-1β is at least 3.9 ng/L and the concentration of TNF-α is at least 11.5 ng/L.

In another general aspect, a visco-supplement composition according to the present invention comprises a processed transcellular fluid having increased concentrations of lipids as compared to the unprocessed transcellular fluid. According to embodiments of the present invention, the concentrations of at least one of fatty acids, cholesterol, and phospholipids in the processed transcellular fluid are increased as compared to their respective concentrations in the unprocessed transcellular fluid. In preferred embodiments of the invention, the processed transcellular fluid comprises fatty acids at a concentration of about 0.25 g/L to about 6.5 g/L; cholesterol at a concentration of about 0.5 g/L to about 9.5 g/L; and/or phospholipids at a concentration of about 0.003 g/L to about 0.3 g/L.

In yet another general aspect, a visco-supplement composition according to the invention comprises a processed transcellular fluid having increased concentrations of carbohydrates as compared to the unprocessed transcellular fluid. According to embodiments of the present invention, the concentrations of one or more of glucose, fructose, hyaluronic acid, and lubricin in the processed transcellular fluid are increased as compared to their respective concentrations in the unprocessed transcellular fluid. Lubricin (proteoglycan 4) is a proteoglycan present in synovial fluid that acts as lubricant. These carbohydrates function to provide lubrication, protection and shock absorption, particularly to inflamed joints. In preferred embodiments of the present invention, the processed transcellular fluid comprises glucose at a concentration of about 600 mg/L to about 900 mg/L; fructose at a concentration of about 48 mg/L to about 59 mg/L; hyaluronic acid at a concentration of about 30 μg/L to about 3600 μg/L; and/or lubricin at a concentration of about 10 μg/ml to about 200 μg/ml.

And in yet another general aspect, a visco-supplement composition according to the present invention comprises a processed transcellular fluid having decreased concentrations of non-protein nitrogenous compounds as compared to the unprocessed transcellular fluid. In particular, the concentrations of one or more of urea, uric acid, and creatinine in the processed transcellular fluid are decreased as compared to their respective concentrations in the unprocessed transcellular fluid. According to preferred embodiments of the present invention, the concentration of urea is no more than 160 mg/L, the concentration of uric acid is no more than 80 g/L, and/or the concentration of creatinine is no more than 14 mg/L in the processed transcellular fluid used in the visco-supplement of the present invention.

According to embodiments of the present invention, the pH of a visco-supplement composition ranges from a pH of about 6.0 to a pH of about 8.0, such as 6.0, 6.5, 7.0, 7.5, or 8.0. Preferably, the pH ranges from 6.5 to 7.5, and is more preferably 7.0.

Embodiments of the present invention also relate to visco-supplement compositions comprising a processed transcellular fluid having optimized concentrations of inorganic constituents and optimized partial pressures of gases, such that the concentrations and partial pressures closely approximate the concentrations of these components in the native synovial fluid. Such inorganic constituents include sodium, potassium, and chloride, and such gases include oxygen and carbon dioxide.

The visco-supplement compositions of the present invention can further comprise additional substances including pharmaceutically acceptable excipients, such as thickeners, salts, preservatives, colorants, etc.; substances to prevent the growth of microbes, such as antifungal, antibacterial, or antiviral agents; and agents that improve the viscosity or thickness of the composition. These additions can be made, provided that they do not cause irritation of the joint, or interfere with the healing properties of the transcellular fluid. The visco-supplement compositions of the present invention can also further comprise one or more pharmaceutically active ingredients, such as an analgesic, an anti-inflammatory agent, an anti-microbial agent, etc.

According to embodiments of the present invention, the visco-supplement composition can further comprise a cryoprotectant. Any cryoprotectant suitable for pharmaceutical use known to those skilled in the art in view of the present disclosure can be used in the composition of the present invention. Examples of cryoprotectants that can be used in the visco-supplement compositions of the present invention include, but are not limited to, dimethyl sulfoxide (DMSO), sucrose, glycerol, glucose, and any other sugars, e.g., monosaccharides or disaccharides, alcohols and penetrating agents, or combinations thereof, routinely used as cryoprotectants by those skilled in the art, which will be know to those skilled in the art in view of the present disclosure. In certain embodiments of the invention, the visco-supplement composition is cryopreserved.

A visco-supplement composition according to a preferred embodiment of the present invention is shown in Table 1 below. The transcellular fluid used in the composition is processed human amniotic fluid.

TABLE 1

Concentrations of inorganic constituents, gases, proteins, carbohydrates, lipids, and non-protein nitrogenous compounds in a visco-supplement composition according to an embodiment of the present invention.

| Component | Unprocessed Transcellular Fluid[1] (Amniotic Fluid) | Composition Target Ranges post-processing High | Composition Target Ranges post-processing Low | Discussion and Function |
|---|---|---|---|---|
| Inorganic Constituents | | | | |
| Sodium | 127 mEq/L | 148.375 | 85.625 | Stay within proscribed range |
| Potassium | 4.0 mEq/L | 48.125 | 21.875 | Increase from about 4.0 mEq/L in source material to a minimum of 21.875 mEq/L |
| Chloride | 105 mEq/L | 145.75 | 66.25 | Stay within proscribed range |
| Calcium | 4.0 mEq/L | 7.21875 | 3.28125 | Stay within proscribed range |
| Magnesium | 1.4 mEq/L | 2.75 | 1.25 | Stay within proscribed range |
| Phosphorus | 29.0 mg/L | 55 | 25 | Increase the amount of phosphorus to the proscribed range |
| Gases/H+ | | | | |
| pH | 7.0 | 7.9375 | 6.125 | In order to restore the proper acid/base balance in an acidic and arthritic joint, stay within the proscribed range |
| PO2 | 2-15 mm Hg | 78 | 8 | in order to provide the proper oxygenation range for use as a visco-supplement in a arthritic joint, increase to the two proscribed ranges |
| PCO2 | 57 mm Hg | 150 | 34 | |
| Protein (Total) | 22-31 g/L | 50.375 | 30.25 | Increase the amount of protein to the proscribed range |
| Albumin | 60% | | 60% | Ensure that Albumin comprises no less than 60% of the protein content |
| α-globulins | 12% | 18% | 12% | Stay within proscribed range |
| β-globulins | 16% | 27% | 16% | Stay within proscribed range |
| γ-globulins | 12% | 18% | 12% | Stay within proscribed range |
| Cytokines | | | | |
| IL-6 | 329 ng/L | | 329 ng/L | No less than the proscribed amount |
| IL-8 | 421 ng/L | | 421 ng/L | No less than the proscribed amount |
| IL-1β | 3.9 ng/L | | 3.9 ng/L | No less than the proscribed amount |
| TNF-α | 11.5 ng/L | | 11.5 ng/L | No less than the proscribed amount |
| C-reactive protein (CRP) | 5.4 mg/L | | | May be present or may be eliminated in any embodiment of the invention |
| Procalcitonin | 1.8 μg/L | | | May be present or may be eliminated in any embodiment of the invention |
| Calprotein | 3425 μg/L | | | May be present or may be eliminated in any embodiment of the invention |
| Non-Protein Nitrogen Compounds | | | | These by-products of metabolism are reduced in the final supplement fluid. |

TABLE 1-continued

Concentrations of inorganic constituents, gases, proteins, carbohydrates, lipids, and non-protein nitrogenous compounds in a visco-supplement composition according to an embodiment of the present invention.

| Component | Unprocessed Transcellular Fluid[1] (Amniotic Fluid) | Composition Target Ranges post-processing High | Composition Target Ranges post-processing Low | Discussion and Function |
|---|---|---|---|---|
| Urea | 370 mg/L | 160 | 82.5 | Reduce qualities such that the amounts are no more than the maximum amount proscribed |
| Uric Acid | 50 mg/L | 80 | 22.5 | Reduce quantities such that the amounts are no more than the maximum amount proscribed |
| Creatinine | 28 mg/L | 14 | 8.75 | reduce quantities such that the amounts are no more than the maximum amount proscribed |
| Carbohydrates | | | | These carbohydrates are important to supply proper levels of nutrients, lubrication, compression and shear resistance and cushioning to the living musculoskeletal joint |
| Glucose | 330 mg/L | 900 | 600 | Increase quantity to the proscribed ranges |
| Fructose | 35 mg/L | 58.625 | 48.125 | Increase quantity to the proscribed ranges |
| Lactic Acid | 370-750 mg/L | 250 | 156.25 | Reduce quantities such that the amounts are no more than the maximum amount proscribed |
| Pyruvate | 8 mg/L | 13.4 | 11 | Increase quality to the proscribed ranges |
| Hyaluronan: mean (SD) | 22.67(10.8)/1.1(0.46) µg/L | 3600 µg/ml | 30 µg/L | Provides Compression & Shear Resistance and is a carries for surface active phospholipids (SAPL), which are a boundary lubricant in visco-supplement fluids. Increase to levels within the proscribed levels. |
| Lubricin (PRG4) | | 200 µg/ml | 10 µg/ml | This is a protein which is related to MCF and is likely carries for SAPL. Increase quantity to the proscribed levels. |
| Total Lipids | 0.48 g/L | | | |
| Fatty Acids | 0.24 g/L | 6.50 g/L | 0.25 g/L | Increase quantity to the proscribed ranges |
| Cholesterol | 0.02 g/L | 9.50 g/L | 0.50 g/L | Increase quantity to the proscribed ranges |
| Phospholipids (Total) | 0.03 g/L | 0.30 mg/ml | 0.003 g/L | Increase quantity to the proscribed ranges |

[1]Referece (1)-(10) were used to determine the quantities of the components in the unprocessed amniotic fluid The transcellular fluid used to produce the visco-supplement compositions of the present invention is isolated or obtained from a donor. As used herein, the term "donor" refers to a mammal from which a transcellular fluid has been obtained or will be obtained. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably a human.

According to preferred embodiments of the present invention, a donor is a human, bovine, or porcine, most preferably a human.

Methods of obtaining a transcellular fluid, such as a human amniotic fluid, or a human aqueous humor or vitreous humor fluid, from a donor using the appropriate sterile techniques are well known to those of ordinary skill in the art. One of ordinary skill in the art would also be familiar with procedures for safely and humanely obtaining the transcellular fluid. For example, human amniotic fluid can be obtained from a donor who is undergoing an amniocentesis procedure, Caesarean section delivery, or vaginal birth using a specially designed receptacle to collect the fluid after rupture of membranes. Amniotic fluid isolated from a donor undergoing a Caesarean delivery is preferred, because red blood cell count can be minimized in this way. However, amniotic fluid obtained from a donor undergoing vaginal birth or Caesarean section can be used with the present invention. Other techniques for isolating transcellular fluids, such as ocular fluid or cerebrospinal fluid include simple needle aspiration.

According to embodiments of the present invention, the transcellular fluid is free of particulate matter, such as cellular debris and tissue debris. Particulate matter can be removed from the transcellular fluid by any method known in the art for removing particulate matter from biological samples, including but not limited to filtration and centrifugation. Particulate matter can be removed at any time after the transcellular fluid has been collected. Preferably, the particulate material is removed prior to any other processing or treatment steps.

According to embodiments of the present invention, the processed transcellular fluid is prepared from an unprocessed transcellular fluid, e.g., by removing non-protein nitrogenous compounds, such as uric acid, urea, creatinine, and nitrogen. These non-protein nitrogenous compounds can be removed by any method known in the art, such as by means of a semi-permeable membrane or filter, or by dialysis. Other suitable means for removing these compounds include osmotic, centrifugal, gravitational or mechanical pumping forces. The transcellular fluid can also be processed to increase the concentration of one or more of proteins, carbohydrates, lipids, and other desirable components using any technique known to those of ordinary skill in the art in view of the present disclosure. For example, a desirable endogenous component can be enriched by filtration or centrifugation with specific parameters. An exogenous desirable component can also be added to the processed transcellular fluid.

For example, using an ultrafiltration approach, a semi-permeable container is filled with raw transcellular fluid, and then a pressure gradient is applied across the semi-permeable membrane using any number of techniques known to those skilled in the art including, but not limited to, a high permeability dialyzer. As another illustrative example, when employing hemodialysis techniques, an electrolyte solution (dialysate) can be applied on one side of a membrane, creating a concentration gradient, which causes water and other non-protein cellular components of the transcellular fluid to flow through the semi-permeable membrane. As yet another illustrative example, rapid ultrafiltration approaches can be used. Rapid ultrafiltration approaches employ a semi-permeable membrane cylindrical container that rotates constantly in order to avoid filter clogging even as a pressure gradient is applied to the contained fluid—either from within the container (pushing), or from the opposite side of the semi-permeable membrane (pulling).

The transcellular fluid can also be concentrated by removal of water using any technique known to those of ordinary skill in the art. For example, substantially all of the water can be removed by lyophilization, etc., or the amount of water can simply be reduced by vacuum filtration, etc.

The transcellular fluid used in the present invention can be further treated in order to promote preservation, lengthen shelf life, etc. These treatments include, but are not limited to sterilization, e.g. gamma-irradiation; and cooling, refrigeration and freezing, addition of one or more preservatives, antimicrobial agents, etc.

Risk assessment is conducted on potential donors with informed consent prior to collection of a transcellular fluid to evaluate the donor's risk factors for communicable diseases such as such as human immunodeficiency virus (HIV), hepatitis B virus (HBV), hepatitis C virus (HCV), cytomegalovirus (CMV), human T-lymphotropic virus (HTLV), syphilis, etc. Potential donors with high risk factors for the communicable diseases are excluded. For example, if an amniotic fluid is to be obtained, risk assessment can be conducted on a pregnant female to evaluate her risk factor for communicable diseases. Medical and social histories of the pregnant female, including physical exam record, and/or risk assessment questionnaire are reviewed, and pregnant females with high risk factors for the communicable diseases are excluded.

Consent to draw blood at the time of obtaining the transcellular fluid, and 1 to 12 months after the transcellular fluid is initially collected from the donors with low risk factors for communicable diseases is obtained. Screening tests on communicable diseases, such as HIV 1 and 2, HCV, Hb Core, syphilis, HTLV I/II, CMV, hepatitis B and C, can be conducted by conventional serological tests on the blood sample drawn at the time the transcellular fluid is obtained. These initial screening tests are preferably completed within seven days after obtaining the transcellular fluid. Preferably, the screening tests are conducted again on a second blood sample collected a few months after the transcellular fluid is obtained, to verify the previous screening results and to allow for detection of communicable diseases acquired shortly before obtaining the transcellular fluid, but tested as "negative" on the previous screening tests. The second blood sample can be collected one to twelve months after obtaining the transcellular fluid, and is preferably collected six months after obtaining the transcellular fluid.

According to preferred embodiments, only donors with informed consent who tested negative for communicable diseases are approved as transcellular fluid donors. According to other preferred embodiments, only donors with informed consent who tested negative for the communicable diseases in both screening tests with blood sample drawn at the time the transcellular fluid is obtained and blood sample drawn one to twelve months after the transcellular fluid is obtained, preferably six months after, are approved as transcellular fluid donors.

The unprocessed transcellular fluid for use in the present invention can also be screened after collection to ensure that it is not contaminated with any communicable disease agents, such as human immunodeficiency virus (HIV), hepatitis B virus (HBV), hepatitis C virus (HCV), cytomegalovirus (CMV), human T-lymphotropic virus (HTLV), syphilis, etc.

Embodiments of the present invention also relate to methods of treating inflammatory conditions of the musculoskeletal system, and methods of increasing joint lubrication using a visco-supplement composition according to an embodiment of the present invention.

According to embodiments of the present invention, a method of treating an inflammatory condition of a musculoskeletal system comprises injecting a visco-supplement composition as described herein into the musculoskeletal system of a subject, such as injection into a joint. Examples of joints into which a visco-supplement composition of the present invention can be injected include all synovial joints, such as hinge joints (e.g., elbow and knee), pivot joints (e.g., atlas and axis bones at the top of the neck), ball and socket joints (e.g., hip), saddle joints (e.g., carpometacarpal joint of the thumb), condyloid joints (e.g., wrist, metacarpophalangeal joints, metatarsophalangeal joint), and gliding joints (e.g., intercarpal joints in the wrist). Other examples of joints into which a visco-supplement composition of the present invention can be injected include all amphiarthoses joints, such as intervertebral discs.

As used herein, "subject" means any animal, preferably a mammal, most preferably a human, to who will be or has been administered a visco-supplement composition according to the present invention.

As used herein, the terms "treat," "treating," and "treatment" are all intended to refer to an amelioration or reversal of at least one measurable physical parameter related to an inflammatory condition of the musculoskeletal system, which is not necessarily discernible in the subject. The terms "treat," "treating," and "treatment" can also refer to preventing the progression, or at least slowing down the progression of the inflammatory condition of the musculoskeletal system. In one embodiment, "treat," "treating," and "treatment" refer to a reduction or complete alleviation of pain associated with the inflammatory condition of the musculoskeletal system. In another embodiment, "treat," "treating," and "treatment" refer to a reduction of joint inflammation. In yet another embodiment, "treat," "treating," and "treatment" refer to an alleviation of one more symptoms associated with joint inflammation, such as joint pain, joint swelling, joint stiffness, and difficulty in joint movement.

As used herein "an inflammatory disorder of the musculoskeletal system" refers to any disease, disorder, or condition characterized by inflammation of a part of the musculoskeletal system. The musculoskeletal system is comprised of joints, tendons, bone, and cartilage. Examples of inflammatory diseases of the musculoskeletal system include, but are not limited to joint inflammation, such as arthritis, particularly osteoarthritis and rheumatoid arthritis; bursitis; bone infection (osteomyelitis); tendonitis; inflammation of the cartilage, such as chondromalacia patellae; and chronic conditions that cause inflammation of the musculoskeletal system, and particularly joints, such as fibromyalgia and Lupus.

According to preferred embodiments of the present invention, the inflammatory disorder of the musculoskeletal system to be treated is joint inflammation. In a particularly preferred embodiment, the joint inflammation is inflammation of a synovial joint, such as a knee joint, a wrist joint, a shoulder joint, a hip joint, or an elbow joint, and is most preferably a knee joint. Because the visco-supplement compositions of the present invention contain many of the same components as the synovial fluid found in healthy joints, the compositions are particularly suited for covering, lubricating, protecting and relieving joint inflammation when injected into the intra-articular space of the joint.

A method of lubricating a joint according to embodiments of the present invention comprises injecting a visco-supplement composition as described herein into an intra-articular space of the joint. The intra-articular space refers to the space inside of a joint between two bones that is usually contained by the articular capsule. The articular capsule, also referred to as the joint capsule, is the envelope surrounding a synovial joint. Preferably the joint to be lubricated is a synovial joint, and is more preferably a knee joint. In a preferred embodiment, a subject is in need of joint lubrication to reduce pain associated with joint movement. In another embodiment of the present invention, the visco-supplement composition is applied to the subject in combination with another treatment for the inflammatory disorder of the musculoskeletal system. Examples of other treatment for the inflammatory disorder of the musculoskeletal system that can be used in combination with the visco-supplement composition include, but are not limited to, general exercise; strengthening exercises; walking aids such as canes or crutches; wheeled walkers or frames; knee bracing; orthotics; non-steroidal anti-inflammatory drugs (NSAIDs); thermal treatments including heat therapy; cryotherapy; transcutaneous electrical nerve stimulation; and acupuncture.

In a particular embodiment, the present invention provides a method of treating joint inflammation in a knee in a subject in need thereof comprising administering a visco-supplement composition of the present invention, wherein the administration comprises intra-articular injection to the knee. Any of the visco-supplement compositions described herein can be used, and preferably the visco-supplement composition comprises a processed human amniotic fluid.

According to embodiments of the invention, the visco-supplement composition can be cryopreserved prior to administration, e.g., injection. Any of the methods of treating an inflammatory condition of a musculoskeletal system, e.g., joint inflammation and particularly joint inflammation of the knee, and any of the methods of lubricating a joint in a subject according to embodiments of the present invention, wherein the visco-supplement composition is cryopreserved prior to injection, can further comprise a step of warming the visco-supplement composition to a temperature in a range of about 15° C. to 25° C., such as 15, 16, 17, 18, 19, 20, 21, 22, 23, 24, or 25° C. before administering the composition to the subject. Preferably, the composition is warmed to a temperate of about 20° to 22° C.

According to embodiments of the present invention, the visco-supplement compositions described herein can be used directly in a method of the present invention. Alternatively, the visco-supplement compositions can be diluted by about 10%-50%. Any diluent known to those of ordinary skill in the art can be used to dilute the visco-supplement composition, such as physiologically compatible saline solution, balanced saline solution, sodium hyaluronate, methylcellulose, dimethylsulfoxide, or any other cryopreservant.

The following examples of the present invention are to further illustrate the nature of the invention. It should be understood that the following examples do not limit the invention and that the scope of the invention is to be determined by the appended claims.

EXAMPLES

Example 1: Clinical Study Evaluating the Efficacy of a Visco-Supplement Composition of the Present Invention in Treating Osteoarthritis Approximately two hundred seventy five (275) patients diagnosed with osteoarthritis of the knee each received a single injection of a visco-supplement composition derived from a human amniotic fluid according to the present invention. The visco-supplement composition was cryopreserved at −150° C., and then warmed to about 20° C. to 22° C. in the clinic prior to injection. The visco-supplement composition (4 mL) was then injected into the articular capsule of the knee joint. The pain level of each of the patients was determined at intervals of thirty days, ninety days, and six months after the initial injection, as measured by the Visual Analog Scale (VAS) and Western Ontario and McMaster Universities Arthritis Index (WOMAC). VAS and WOMAC are a set of standardized questions widely used by health professionals to evaluate the condition of patients with osteoarthritis of the hip and knee, by asking a set of questions to assess pain, stiffness, and physical function.

The results of the clinical study are shown below in Table 2, referred to as "Study A." Also shown in Table 2 are the reported results of similar studies conducted with non-human derived hyaluronic acid (Studies B, C, and D), and corticosteroid visco-supplements (Studies E, F, and G) for comparison. In the reported studies, pain relief from the hyaluronic acid visco-supplement and corticosteroid injections was also evaluated using VAS and WOMAC. Briefly, the reported data in the Table for Studies B-G was obtained as follows: Study B was the therapeutic trajectory following intra-articular hyaluronic acid injection in knee osteoarthritis (meta-analysis); Study C evaluated the efficacy of a single intra-articular injection of Gel-200 (cross-linked formulation of hyaluronic acid) in treating symptomatic knee osteoarthritis in a multicenter randomized controlled trial; Study D evaluated the efficacy of Sinovial.® (purified intra-articular hyaluronic acid) and Synvisc.® (hylan G-F20) in the treatment of symptomatic knee osteoarthritis; Study E evaluated the efficacy of intra-articular corticosteroid injections in treating knee osteoarthritis; Study F evaluated pain relief after steroid injection in the knee of patients with rheumatoid knee; and Study G was a randomized trial evaluating the efficacy of intra-articular injections of a composition of hyaluronic acid, corticosteroid, and isotonic saline in treating hip osteoarthritis.

TABLE 2

Comparison of pain relief and adverse events experienced by patients having joint inflammation and treated with injections of either a visco-supplement composition of the present invention, a hyaluronic acid derived injection, or corticosteroid injection.

|  | Processed Amniotic Fluid Visco-supplement of the invention | Hyaluronic Acid (non-human derived) Injection Studies | | | Corticosteroid Injection Studies | | |
|---|---|---|---|---|---|---|---|
|  | Study A | Study B | Study C | Study D | Study E | Study F | Study G |
| Number of patients | 275 | 44 | 379 | 381 | 28 RCT (1973 patients)[1] | 300 | 101 |
| % pain relief (VAS, WOMAC) | 61%% (at 30 days) 53% (at 180 days) | 31% (at 30 days) | 41% (overall) | 54% (overall) | 22% (overall) | 18% (overall) | 27% (overall) |
| Adverse Events | None reported | N/A | Joint swelling, effusions, arthralgia | Injection site hematoma, injection site, pain, arthralgia, and joint swelling | None reported | None reported | None reported |

[1] "28 RCT (1973 patients)"-refers to twenty-eight randomized control tests (RCT) representing an aggregate of 1,973 patients.

From the results of the clinical study reported in Table 2, it can be seen that the visco-supplement composition according to an embodiment of the present invention was highly efficacious in relieving pain in patients with knee osteoarthritis, with patients reporting 61% improvement in pain thirty days after the initial injection. The pain relief continued with an average 53% rate of pain relief after six months following the initial injection. Importantly, 84.65% of the patients reported 40% or greater pain improvement based on total WOMAC score at 30 days. The visco-supplement composition of the present invention was also highly tolerated by patients, as evidenced by the fact that adverse events were 2.5%, but were related to injection site pain and resolved rapidly. Moreover, comparing the results of the study with the visco-supplement composition of the present invention to those of studies conducted with non-human derived hyaluronic acid and corticosteroid injections, the composition of the present invention has increased efficacy and tolerability in patients.

The results of the clinical study indicate that the visco-supplement composition of the present invention is highly efficacious for treating inflammation of the musculoskeletal system, and particularly joint inflammation. The results also indicate that the visco-supplement composition is highly tolerated in patients, with low adverse side effects reported up to thirty days after the initial injection.

Accordingly, the visco-supplement composition of the present invention provides a promising new treatment for joint inflammation having improved safety and efficacy.

Example 2: Additional Clinical Studies Evaluating the Efficacy of a Visco-Supplement Composition of the Present Invention in Treating Osteoarthritis This study included one hundred sixty two (162) patients diagnosed with Grade 1-3 knee osteoarthritis as determined using the radiologic Kellgren-Lawrence scale. The Kellgren-Lawrence scale is a scoring tool used to assess the severity of knee osteoarthritis on a radiograph. A score of Grade 0 indicates no radiographic features of osteoarthritis; Grade 1 indicates possible joint space narrowing and osteophyte formation; Grade 2 indicates definite osteophyte formation with possible joint space narrowing; Grade 3 indicates multiple osteophytes, definite joint space narrowing, sclerosis, and possible bony deformity; and Grade 4 indicates large osteophytes, marked joint space narrowing, severe sclerosis and definite bony deformity.

In this study, each patient received a single injection of a visco-supplement composition derived from a human amniotic fluid according to the present invention. The visco-supplement composition was cryopreserved at −150° C., and then warmed about 20° C. to 22° C. in the clinic prior to injection. The visco-supplement composition (4 mL) was then injected into the articular capsule of the knee joint. The pain level of each of the patients was determined at intervals of thirty days, ninety days and six months after the initial injection, as measured by the Visual Analog Scale (VAS) and Western Ontario and McMaster Universities Arthritis Index (WOMAC).

VAS and WOMAC was measured at baseline, and again at ninety days (90 days) after the initial injection. The results of this study are reported as percent average improvement. The WOMAC results, which are shown in Table 3 below, are reported separately for two subscales (WOMAC Pain 500 mm, and WOMAC Difficulty 1700 mm), and also for the sum of these two subscales (WOMAC 2400 mm). The absolute average values for base-line and improvement after 90 days for the VAS and WOMAC scales are reported in millimeters (mm), which is customary practice for researchers and clinicians.

TABLE 3

WOMAC and VAS scores reported 90 days after initial injection
(values are the average of data from 162 patients total)

| | 90- day ($t_{90}$) Results After Initial Injection | | | | |
|---|---|---|---|---|---|
| | 90 day ($t_{90}$) Avg | 90 day ($t_{90}$) Avg improved from $t_0$ | 90 day ($t_{90}$) Avg % improved from $t_0$ | 90 day ($t_{90}$) % over 40% improved from $t_0$ | 90 day ($t_{90}$) % over 75% improved from $t_0$ |
| WOMAC (2400 mm) | 366.17 ± 473.43 153 (0-2246) | −686.91 ± 501.75 −590.5 (−2122-445) | 65.23% | 82.10 | 54.94 |
| WOMAC DIFFICULTY (1700 mm) | 256.05 ± 336.30 99.5 (0-1616) | −486.29 ± 367.62 −435.5 (1533-305) | 65.51% | 81.48 | 55.56 |
| WOMAC STIFFNESS (200 mm) | 34.64 ± 46.48 14 (0-197) | −64.02 ± 54.05 −67 (−181-106) | 64.90% | 79.63 | 61.11 |
| WOMAC PAIN (200 mm) | 75.48 ± 98.76 34.5 (0-433) | −136.60 ± 111.00 −1.09 (−459-119) | 64.41% | 77.78 | 54.94 |
| VAS | 20.33 ± 24.16 10.5 (0-100) | −3489 ± 27.39 −36 (100-36) | 63.18% | 75.93 | 54.32 |

As shown by the data in Table 3 above, ninety days after treatment a significant number of patients participating in the study reported over 40% improvement (over 80% as determined by aggregated WOMAC scores; and 76% as determined by VAS scores).

Moreover, only 4 of the 162 total patients reported any adverse side effects after 90 days. Arthralgia (pain in the knee joint) is the most common treatment-related side effect in hyaluronic acid studies, and is typically reported as an acute (immediate) or near-acute adverse event. In contrast to the observations in the clinical study with the visco-supplement composition of the present invention, such adverse events have typically been reported in treatment studies with other visco-supplement compositions, such as, or example Orthotics (12.6%), Euflexxa (9.2%), GelOne (17.7%), Monovisc (5.0%), and Synvisc (7.0%), Durolane/Supartz (17.2%) (data obtained from online PubMed Database of Clinical Studies).

Taken together, the above results demonstrate that compositions of the present invention can be used to effectively treat diseases, disorders, and conditions of the musculoskeletal system, such as osteoarthritis, with very low reported adverse side effects, and with significant improvement observed only a few weeks after a single injection.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

1. Assali N A: Biology of Gestation, Vol 1, p 276, New York, Academic Press, 1968 unless noted otherwise.
2. Engstrom-Laurent A and T C Laurent. Clinical Impact of Bone and Connective Tissue Markers Pg 237 Academic Press 1989 (AF values are for 16 weeks and 39 weeks gestation, respectively).
3. Laurent U B G, R K Reed. Advance Drug Delivery Reviews 7:237-256 (1991)
4. Cajori A F. J Biol Chem. 76:471-480 (1928)
5. Treuhaft P S and D J McCarty Arthritis & Rheumatism 14(4):475-484 (1971)
6. Osteoarthritis: Diagnosis and Medical/Surgical Management (Moskowitz ed.), pg 207 Lippincott Williams & Wilkins (2007)
7. Bole G G. Arthritis and Rheumatism 5(6):589-601 (1962)
8. Wilson S E et al. IOVS 30(3):449-453 (1989)
9. Cenedella R J. Biochimica et Biophysic Acta 793:448-454 (1984)
10. Schmidt T A et al. JAMA Ophthalmol 131(6):766-776 (2013)
11. Murphy et al. Arthritis Rheum 2008; 59(9):1207-1213.
12. Murphy et al. Osteoarthritis Cartilage 2010; 18(11): 1372-9.

What is claimed is:

1. A method of treating an inflammatory condition of a musculoskeletal system in a subject in need thereof comprising injecting a visco-supplement composition into the musculoskeletal system of the subject wherein the visco-supplement composition includes a processed transcellular fluid, the processed transcellular fluid including 30.25 g/L to 50.375 g/L of proteins, 0.25 g/L to 6.5 g/L of fatty acids, 0.5 g/L to 9.5 g/L of cholesterol, 0.003 g/L to 0.3 g/L of phospholipids, glucose at a concentration of 600 mg/L to 900 mg/L, fructose at a concentration of 48 mg/L to 59 mg/L, hyaluronic acid at a concentration of 30 µg/L to 3600 µg/L, lubricin at a concentration of 10 µg/ml to 200 µg/ml, no more than 160 mg/L of urea, and no more than 80 g/L of uric acid and no more than 14 mg/L of creatinine.

2. The method according to claim 1, wherein the inflammatory condition is joint inflammation.

3. The method according to claim 1, wherein the inflammatory condition is selected from the group consisting of osteoarthritis, rheumatoid arthritis, fibromyalgia, Lupus, bursitis, osteomyelitis, tendinitis, and chondromalacia patellae.

4. The method according to claim 1, wherein the composition has a pH in a range of about 6.0 to about 8.0.

5. The method according to claim 1, wherein the processed transcellular fluid includes at least 329 ng/L of IL-6, at least 421 ng/L of IL-8, at least 3.9 ng/L of IL-10 and at least 11.5 ng/L of TNF-α.

6. The method according to claim 1, wherein the processed transcellular fluid includes (a) an increased concentration of at least one of a first component selected from the group consisting of proteins, lipids, and carbohydrates as compared to a concentration of the first component in an unprocessed transcellular fluid; and (b) a decreased concentration of at least one of a second component selected from the group consisting urea, uric acid, and creatinine, as compared to a concentration of the second component in the unprocessed transcellular fluid.

7. The method according to claim 1, wherein the composition is substantially free of particulate matter.

8. A method of treating an inflammatory condition of a musculoskeletal system in a subject in need thereof comprising:
   injecting a visco-supplement composition into the musculoskeletal system of the subject wherein the visco-supplement composition includes a processed transcellular fluid including:
   (a) an increased concentration of at least three of a first component selected from the group consisting of 30.25 g/L to 50.375 g/L of proteins, 0.003 g/L to 0.3 g/L of phospholipids, 0.25 g/L to 6.5 g/L of fatty acids, 0.5 g/L to 9.5 g/L of cholesterol, glucose at a concentration of 600 mg/L to 900 mg/L, fructose at a concentration of 48 mg/L to 59 mg/L, hyaluronic acid at a concentration of 30 µg/L to 3600 µg/L, lubricin at a concentration of 10 µg/ml to 200 µg/ml, as compared to a concentration of the first component in an unprocessed transcellular fluid; and
   (b) a decreased concentration of at least two of a second component selected from the group consisting of no more than 160 mg/L of urea, no more than 80 g/L of uric acid, and no more than 14 mg/L of creatinine, as compared to a concentration of the second component in the unprocessed transcellular fluid.

9. The method of claim 8, wherein the wherein the composition has a pH in a range of about 6.0 to about 8.0.

10. The method of claim 8, wherein the wherein the composition is substantially free of particulate matter.

11. The method of claim 8, wherein the processed transcellular fluid includes at least four of the first component.

12. The method of claim 11, wherein the processed transcellular fluid includes three of the second component.

13. The method of claim 8, wherein the processed transcellular fluid includes at least five of the first component.

14. The method of claim 13, wherein the processed transcellular fluid includes three of the second component.

15. The method of claim 8, wherein the processed transcellular fluid includes at least six of the first component.

16. The method of claim 15, wherein the processed transcellular fluid includes three of the second component.

17. The method of claim 8, wherein the processed transcellular fluid includes at least seven of the first component.

18. The method of claim 17, wherein the processed transcellular fluid includes at least three of the second component.

19. The method of claim 8, wherein the processed transcellular fluid includes 30.25 g/L to 50.375 g/L of proteins, 0.25 g/L to 6.5 g/L of fatty acids, 0.5 g/L to 9.5 g/L of cholesterol, 0.003 g/L to 0.3 g/L of phospholipids, glucose at a concentration of 600 mg/L to 900 mg/L, fructose at a concentration of 48 mg/L to 59 mg/L, hyaluronic acid at a concentration of 30 µg/L to 3600 µg/L, lubricin at a concentration of 10 µg/ml to 200 µg/ml, no more than 160 mg/L of urea, no more than 80 g/L of uric acid and no more than 14 mg/L of creatinine.

* * * * *